United States Patent
Bertrams et al.

(10) Patent No.: US 10,354,410 B2
(45) Date of Patent: Jul. 16, 2019

(54) APPARATUS FOR DETERMINING A POSITION OF A FIRST OBJECT WITHIN A SECOND OBJECT

(75) Inventors: Robert Hendrikus Petrus Bertrams, Eindhoven (NL); Gerardus Henricus Maria Gijsbers, Eindhoven (NL)

(73) Assignee: KONINKLIJKE PHILIPS N.V., Endhoven (NL)

( * ) Notice: Subject to any disclaimer, the term of this patent is extended or adjusted under 35 U.S.C. 154(b) by 1417 days.

(21) Appl. No.: 12/515,855

(22) PCT Filed: Nov. 21, 2007

(86) PCT No.: PCT/IB2007/054731
§ 371 (c)(1),
(2), (4) Date: May 21, 2009

(87) PCT Pub. No.: WO2008/065581
PCT Pub. Date: Jun. 5, 2008

(65) Prior Publication Data
US 2010/0020161 A1    Jan. 28, 2010

(30) Foreign Application Priority Data
Nov. 28, 2006    (EP) .................................... 06124894

(51) Int. Cl.
*H04N 13/00*    (2018.01)
*G06T 7/73*    (2017.01)
(Continued)

(52) U.S. Cl.
CPC .................. *G06T 7/75* (2017.01); *G06T 7/33* (2017.01); *A61B 6/12* (2013.01); *A61B 34/20* (2016.02);
(Continued)

(58) Field of Classification Search
USPC .......................................... 348/45
See application file for complete search history.

(56) References Cited

U.S. PATENT DOCUMENTS 5,172,103 A * 12/1992 Kita ....................... G09G 5/393
345/667
5,297,549 A * 3/1994 Beatty et al. .................. 600/374
(Continued)

FOREIGN PATENT DOCUMENTS

WO    0072264 A1    11/2000
WO    0120552 A1    3/2001
(Continued)

OTHER PUBLICATIONS

Ector et al: "Cardiac Three-Dimensional Magnetic Resonance Imaging and Fluoroscopy Merging a New Approach for Electroanatomic Mapping to Assist Catheter Ablation"; Circulation 2005, vol. 112, pp. 3769-3766.

(Continued)

*Primary Examiner* — Gims S Philippe (57) ABSTRACT

The present invention relates to an apparatus for determining a position of a first object (14) within a second object (13), wherein the first object (14) contacts the second object (13) at a contact region. The apparatus (1) comprises a provision unit (2) for providing a three-dimensional model (20) of the second object (13). A projection unit (5, 6, 7, 21) generates a two-dimensional projection image (26) of the first object (14) and of the second object (13), and a registration unit (8) registers the three-dimensional model (20) with the two-dimensional projection image (26). A determination unit (9) determines the position of the contact region from the position of the first object (14) on the two-dimensional projection image (26) and the registered three-dimensional model (20) of the second object (13), wherein the position (Continued)

of the contact region is the position of the first object (14) within the second object (13).

20 Claims, 5 Drawing Sheets

(51) Int. Cl.
    *G06T 7/33*     (2017.01)
    *A61B 6/12*     (2006.01)
    *A61B 17/00*     (2006.01)
    *A61B 34/10*     (2016.01)
    *A61B 34/20*     (2016.01)
    *A61B 90/00*     (2016.01)

(52) U.S. Cl.
    CPC .......... *A61B 2017/00044* (2013.01); *A61B 2034/102* (2016.02); *A61B 2090/364* (2016.02); *A61B 2090/376* (2016.02); *G06T 2207/10121* (2013.01); *G06T 2207/30021* (2013.01); *G06T 2207/30048* (2013.01)

(56) References Cited

U.S. PATENT DOCUMENTS

| | | | |
|---|---|---|---|
| 5,848,972 A * | 12/1998 | Triedman et al. | 600/508 |
| 6,233,476 B1 | 5/2001 | Strommer et al. | |
| 6,556,695 B1 | 4/2003 | Packer et al. | |
| 7,454,043 B2 | 11/2008 | Eck et al. | |
| 8,515,527 B2 | 8/2013 | Vaillant et al. | |
| 2002/0045809 A1* | 4/2002 | Ben-Haim | 600/374 |
| 2003/0181809 A1 | 9/2003 | Hall et al. | |
| 2006/0241413 A1* | 10/2006 | Boese et al. | 600/431 |
| 2006/0257006 A1 | 11/2006 | Bredno et al. | |

FOREIGN PATENT DOCUMENTS

| | | |
|---|---|---|
| WO | 2005020148 A1 | 3/2005 |
| WO | 2006028824 A1 | 3/2006 |

OTHER PUBLICATIONS

Razavi et al: "Cardiac Catheterisation Guided by MRI in Children and Adults With Congenital Heart Disease"; The Lancet, vol. 362, Issue 9399, pp. 1877-1882, Dec. 2003.

* cited by examiner

APPARATUS FOR DETERMINING A POSITION OF A FIRST OBJECT WITHIN A SECOND OBJECT

FIELD OF THE INVENTION

The invention relates to an apparatus, a method and a computer program for determining a position of a first object within a second object.

BACKGROUND OF THE INVENTION

An apparatus for determining a position of a first object within a second object is, for example, used in the field of cardiac electrophysiology for localizing the three-dimensional position of a catheter tip within a heart of a patient. These localized three-dimensional positions of the catheter tip are used to record locations of interest such as anatomical landmarks and/or ablation locations in the three-dimensional space. This known localization is based on electro-magnetic or ultrasound real time (low latency) three-dimensional localization techniques. For example, an apparatus for localizing the three-dimensional position of a catheter tip comprises three magnetic field emitting coils, which are arranged close to the patient, and a corresponding sensor on the tip of the catheter, wherein the three-dimensional position of the catheter tip is determined by triangulation measurements.

These known techniques for determining a position of a first object like a catheter tip within a second object like a heart of a patient are complex, require a considerable amount of hardware, in particular specialized catheters, and are, therefore, expensive.

SUMMARY OF THE INVENTION

It is an object of the present invention to provide an apparatus, a method and a computer program for determining a position of a first object within a second object, which is less complex, which requires a reduced amount of hardware and which is, therefore, less expensive.

In a first aspect of the present invention an apparatus for determining a position of a first object within a second object is provided, wherein the first object contacts the second object at a contact region, wherein the apparatus comprises:
 a provision unit for providing a three-dimensional model of the second object,
 a projection unit for generating a two-dimensional projection image of the first object and of the second object,
 a registration unit for registering the three-dimensional model with the two-dimensional projection image,
 a determination unit for determining the position of the contact region from the position of the first object on the two-dimensional projection image and the registered three dimensional model of the second object, the position of the contact region being the position of the first object within the second object, wherein the determination unit is adapted such that the position of the contact region is determined by determining the position where a line of sight of the first object intersects a surface of the three-dimensional model.

The invention is based on the idea that the two-dimensional position of the first object, and, thus, of the contact region, within the second object can be determined by using the position of the first object on the two-dimensional projection image and that the position of the first object in the third dimension can be determined from the position of the contact region, which is preferentially a contact point between the first object and the second object, in the third dimension preferentially by using the information that the first object is located on a surface of the registered three-dimensional model. Therefore, the position of the first object within the second object can be determined without the need of a complex localization arrangement, like the three magnetic field emitting coils and the sensor on the catheter tip as in the above described prior art. Thus, the amount of hardware required for determining the position of a first object within a second object is reduced and, thus, the costs of such an apparatus are also reduced.

The provision unit is preferentially a three-dimensional model generation unit for generating a three-dimensional model of the second object from detection data of the second object acquired from a detection data generation unit like a computed tomography system, a magnetic resonance imaging system, a three-dimensional rotational X-ray system or an ultrasound imaging system. The three-dimensional model generation unit is preferentially adapted for generating a three-dimensional model of the second object by using known reconstruction techniques for reconstructing the second object from the acquired detection data, by segmenting the second object in the reconstructed image and by surface rendering the segmented second object.

The first object is preferentially a catheter, which is located within a heart of a patient being the second object. The projection unit is preferentially an X-ray fluoroscopy unit.

It is preferred that the projection unit is adapted for generating two-dimensional projection images in different projection directions and that the registration unit is adapted for registering the three-dimensional model with the different two-dimensional projection images such that in each of the different projection directions the three-dimensional model is registered with the corresponding two-dimensional projection image. Since the different two-dimensional projection images are registered in each of the different projection directions with the three-dimensional model, the two-dimensional projection image is registered with the three-dimensional model in each arbitrarily chosen direction. Thus, the three-dimensional model can be shown on a two-dimensional projection image having an arbitrarily chosen projection direction. Furthermore, the determination of the position of the first object can be performed by using a projection image of an arbitrarily chosen projection direction without the need of registering the three-dimensional model with this two-dimensional projection image again. This reduces the time needed for determining the position of the first object within the second object, if a user wants to determine the position of the first object within the second object after changing the position of the first object and the projection direction.

The line of sight is the line defined by the position of the first object on the two-dimensional projection image and the position of the source of the projection unit, which is preferentially an X-ray source, in particular the focal spot of the X-ray source. This line of sight and the intersection point between this line of sight and the three-dimensional model can easily be determined, which allows determining the position of the first object within the second object with low computational costs.

It is preferred that the apparatus further comprises a selection unit for selecting which of two or more intersection points of the line of sight with the three-dimensional model corresponds to the position of the contact region. It is further preferred that the apparatus comprises an visualization unit for visualizing the three-dimensional model, the line of sight and the two or more intersection points from a side view, and that the selection unit comprises an input unit allowing a user selecting one of the two or more intersection points as the position of the contact region. It is also preferred that the projection unit is adapted for generating at least two two-dimensional projection images of the first object and of the second object in at least two projection directions, that the determination unit is adapted for determining the position of the contact region where a line of sight of the first object with respect to a projection direction of one of the two-dimensional projection images intersects the three-dimensional model, that the selection unit is adapted for selecting which of the two or more intersection points of the line of sight with the three-dimensional model corresponds to the position of the contact region by using at least one of the other two-dimensional projection images. These preferred embodiments for determining the position of a first object within a second object can easily be implemented on a computer system and also require very low computational costs.

The line of side intersects the three-dimensional model generally at two intersection points, in particular, if the three-dimensional model is not very complex. But, in a more complex three-dimensional form of the second object, and therefore of the three-dimensional model, more than two intersection points can exist.

In a further embodiment, the projection unit is adapted for generating at least two two-dimensional projection images of the first object and of the second object in at least two projection directions, wherein the determination unit is adapted for determining at least two line of sights of the first object for the at least two projection directions, wherein the determination unit is further adapted for determining the intersection point of the at least two line of sights, wherein the determination unit is further adapted for moving the intersection point onto a surface of the three-dimensional model, wherein the moved intersection point is the determined position of the contact region. In theory, the intersection point of the at least two line of sights should be located on a surface of the second object, because the first object contacts the second object, but in reality, because of possible inaccuracies of the apparatus for determining the position of the first object within a second object and because of a possible movement of the first object and/or the second object, the intersection point is generally not located on a surface of the second object. Therefore, the intersection point is moved onto a surface of the three-dimensional model of the second object. This allows determining the contact region and therefore the position of the first object within the second object with an improved accuracy, while the required computational costs are still low.

It is preferred that the apparatus comprises a visualization unit for visualizing the three-dimensional model over the two-dimensional projection image, wherein the visualization unit is adapted for showing the three-dimensional model, the two-dimensional projection image and the determined position of the first object simultaneously. It is further preferred that the visualization unit is adapted for visualizing the three-dimensional model and the two-dimensional projection image simultaneously, while the projection unit is generating two-dimensional projection images. It is further preferred that the visualization unit is adapted such that the determined position of the first object can be visualized by a graphical indication on the three-dimensional model. This allows showing the position of the first object within the second object such that it is easily understandable by a user.

It is further preferred that, if the first object is moved to different positions on a surface of the second object, each of these positions is determined, indicated on the three-dimensional model by a graphical indication, and recorded on the three-dimensional model such that the different determined positions, i.e. different graphical indications, e.g. crosses or spheres, form a path along which the first object has been moved along the surface of the second object. If the first object is the tip of an ablation catheter and if the second object a heart of patient, the recorded positions can illustrate e.g. ablation points on the heart wall.

It is further preferred that the visualization unit comprises an imaging region, for visualizing the three-dimensional model over the two-dimensional projection image. This allows illustrating on the imaging region, the complete available information, i.e. the two-dimensional projection image, the three-dimensional model of the second object and preferentially the position of the first object within the second object. It is further preferred that the projection unit, for example, the X-fluoroscopy system, comprises a displaying unit or that the visualization unit comprises a further imaging region for displaying or visualizing the two-dimensional projection image without being disturbed by the three-dimensional model.

It is further preferred that the provision unit is adapted for providing a moving three-dimensional model of the second object, that the apparatus further comprises a motion detection unit for detecting the motion of the second object during generating the two-dimensional projection image of the first object and of the second object by the projection unit, that the registration unit is adapted for registering the moving three-dimensional model with the two-dimensional projection image. This allows determining the position of the first object within the second accurately, even if the second object is moving.

In a further aspect of the present invention a method for determining a position of a first object within a second object is provided, wherein the first object contacts the second object at a contact region, wherein the method comprises following steps:

providing a three-dimensional model of the second object,
generating a two-dimensional projection image of the first object and of the second object,
registering the three-dimensional model with the two-dimensional projection image,
determining the position of the at least one contact region from the position of the first object on the two-dimensional projection image and the registered three-dimensional model of the second object, the position of the at least one contact region being the position of the first object within the second object, wherein the position of the contact region is determined by determining the position where a line of the first object intersects a surface of the three-dimensional model.

In a further aspect of the invention an apparatus for applying energy to a second object via a surface of the second object by using an energy emitting first object is provided, wherein the energy emitting first object contacts the surface of the second object at a contact region and wherein the apparatus for applying energy comprises an apparatus for determining a position of a first object within a second object in accordance with the invention. The apparatus for applying energy is, for example, an ablation apparatus for an ablation treatment of a heart of a patient. In this case, the first object is a tip of an ablation catheter which contacts an inner surface of the heart during the application of energy.

In a further aspect of the invention a computer program for determining a position of a first object within a second object is provided, wherein the computer program comprises program code means for causing an apparatus to carry out a position determination method of the present invention when the computer program is run on a computer controlling the apparatus.

It shall be understood that the apparatuses and the method as claimed in independent claims have similar and/or identical preferred embodiments as defined in the dependent claims. It shall be understood that preferred embodiments of the invention can also be any combination of the dependent claims.

BRIEF DESCRIPTION OF THE DRAWINGS

These and other aspects of the invention will be apparent from and elucidated with reference to the embodiments described hereinafter. In the following drawings.

DETAILED DESCRIPTION OF EMBODIMENTS

Figure 1:
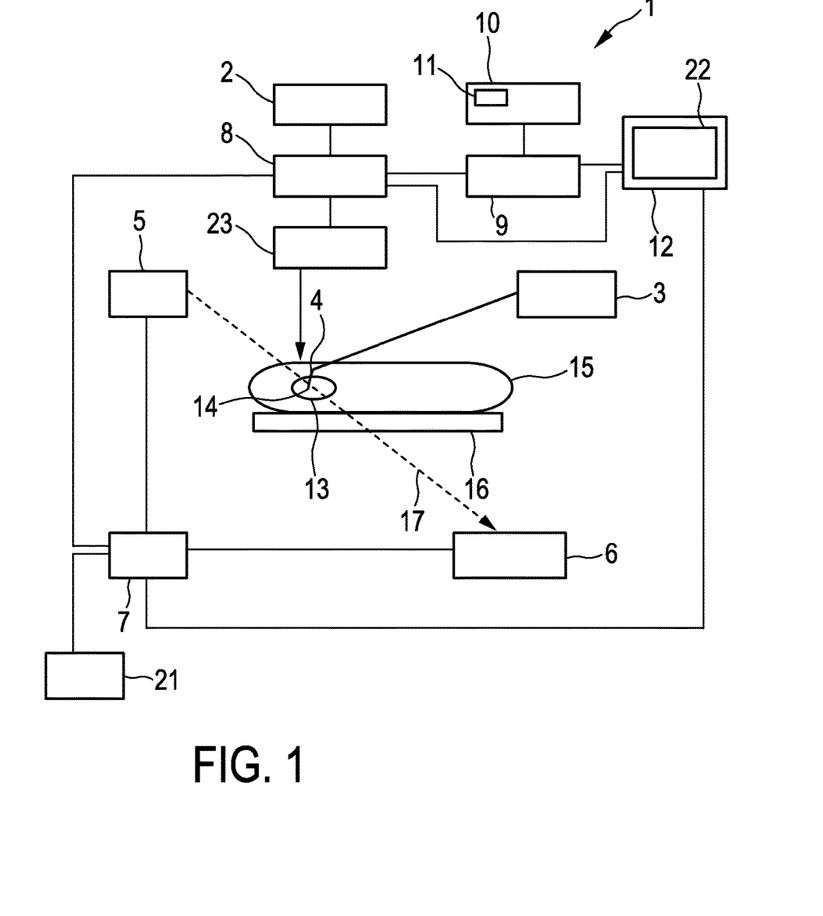
FIG. 1 shows schematically an embodiment of an apparatus for applying energy to a second object via a surface of the second object by using an energy emitting first object.

FIG. 1 shows an apparatus 1 for determining the position of a first object 14 within a second object 13, wherein the first object 14 contacts the second object 13 at a contact region. In this embodiment, the first object is a tip 14 of a catheter 4, for example, for an ablation on an inner wall of the heart 13, which is in this embodiment the second object, of a patient 15. The patient is located on a patient table 16. Thus, in this embodiment, the apparatus 1 is capable of determining the position of the catheter tip 14 on an inner surface of the heart 13. The catheter 4 is preferentially connected to an ablation and sensing unit 3. The combination of the catheter tip 14, the catheter 4 and the ablation and sensing unit 3 is well known and will therefore not be described in detail.

The apparatus 1 comprises an X-ray source 5 for emitting X-rays 17, a detection unit 6 for detecting the X-rays 17 after having traversed the second object 13 and a control unit 7 for controlling the X-ray source 5 and the detection unit 6. The X-ray source 5, the detection unit 6 and the control unit 7 form a projection unit, which is in this embodiment a fluoroscopy device. The projection unit 5, 6, 7 generates two-dimensional projection images of the first object 14 and of the second object 13 and transmits these two-dimensional projection images to a registration unit 8. The registration unit 8 further receives a three-dimensional model of the second object 13 from a provision unit 2. The provision unit 2 can be a memory, in which a three-dimensional model of the second object 13 is stored. Alternatively or in addition, the projection unit 2 can comprise a three-dimensional model generation unit for generating a three-dimensional model of the second object 13. The three-dimensional model generation unit can comprise a detection data generation unit like a computed tomography imaging system, a magnetic resonance imaging system, a three-dimensional rotational X-ray system or an ultrasound imaging system. The three-dimensional model generation unit generates a three-dimensional image of the second object 13 by using the detection data acquired by the detection data generation unit preferentially in advance, i.e. before the first object 14 is located within the second object 13. Preferentially, the second object 13 is segmented within the three-dimensional image, and the segmented second object 13 is visualized by, for example, surface rendering yielding a three-dimensional model of the second object 13. Also, other methods for generating a three-dimensional model of the second object 13 can be used in accordance with the invention.

The registration unit is adapted for registering the three-dimensional model of the second object 13 with the two-dimensional projection image received from the projection unit 5, 6, 7. The registration unit 8 performs the registration of the two-dimensional projection image with the three-dimensional model of the second object 13 by using features, which can be located in both, the two-dimensional projection image and the three-dimensional model of the second object 13. For this 2D-3D registration the method described in Circulation 2005 112:3769-3776 or in Lancet 2003 362:1877-82 can, for example, be used.

The 2D-3D registration can, for example, be performed by using two two-dimensional projection images, which have been generated in different projection directions. The three-dimensional model of the second object 13 can be sized, rotated and translated by means of known graphical techniques such that the three-dimensional model is aligned with one of the two-dimensional projection images by using "fiducial points" (image features that indicate certain anatomical structures or that are visible in both the two-dimensional projection image and the three-dimensional model) or by using an X-ray contrast medium injection to outline the shape of, in this embodiment, the heart chamber under consideration or by putting, in this embodiment, catheters at known positions, or by using, in this embodiment, the spine or ribs that can easily be seen in both, the two-dimensional projection image and the three-dimensional model of the second object 13. Now the alignment is correct in two dimensions being the dimensions of the two-dimensional projection image. The alignment in the dimension perpendicular to these two dimensions is firstly unknown. To find this third dimension, the projection unit is rotated preferably around 90°, and the three-dimensional model is rotated accordingly. The second of the two two-dimensional projection images corresponds to this rotated projection direction, i.e. the second two-dimensional projection image has been generated in this rotated projection direction, and the three-dimensional model is also aligned with respect to this second two-dimensional projection image. In this way, the alignment between the two-dimensional projection image and the three-dimensional model can be established in all three dimensions. If the projection unit is rotated to obtain a new projection direction, the three-dimensional model preferentially automatically rotates with it, as the projection unit automatically sends it position parameters to the registration unit 8. The two-dimensional projection image and the registered three-dimensional model of the second object 13 are preferentially visualized on a visualization unit 12.

The apparatus 1 preferentially further comprises a motion detection unit 23 for detecting the motion of the second object during generating the two-dimensional projection image of the first object 14 and of the second object 13. The motion detection unit 23 is in this embodiment an electrocardiograph, which detects the motion of the heart 13. In other embodiments, the motion detection unit 23 can be an image processing software that analyses the motion of the second object 13 for fluoroscopy in real time (low latency), or a real time ultrasound imaging system for the same. Furthermore, preferentially, the provided three-dimensional model of the second object 13 is a moving three-dimensional model, which can, for example, be generated by a three-dimensional model generation unit comprising a detection data generation unit, an image reconstruction unit, a segmentation unit and a surface rendering unit, wherein during the detection of detection signals for reconstructing the image of the second object 13 the motion of the second object 13 is detected by the motion detection unit 23. If a moving three-dimensional model is provided and if the motion of the second object 13 is detected during generating the two-dimensional projection images, the registration unit 8 is adapted for registering the moving three-dimensional model with the two-dimensional projection image also with respect to the movement of the second object 13.

The visualization unit 12 comprises an imaging region 22. On the imaging region 22 the three-dimensional model 20 of the second object 13 together with the registered two-dimensional projection image is preferentially displayed. Furthermore, the projection unit comprises a display unit 21 for displaying the two-dimensional projection image.

The apparatus 1 further comprises a determination unit 9 for determining a contact region between the first object 14 and the second object 13, wherein the contact region is the position of the first object 14 within the second object 13.

Figure 2:
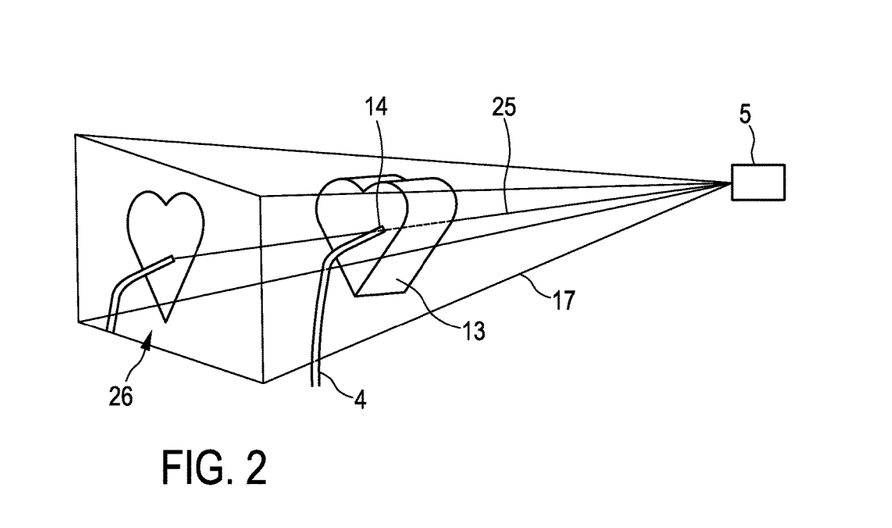
FIG. 2 shows schematically the generation of a two-dimensional projection image.
Figure 3:
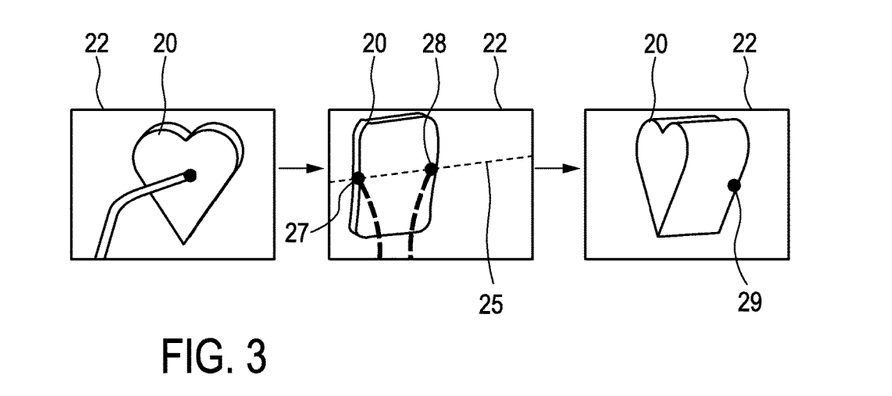
FIG. 3 shows schematically an imaging region of a visualization unit displaying successively a three-dimensional model of the second object in different orientations.

An embodiment of a determination of the contact region will now be described with reference to FIG. 2. FIG. 2 shows the X-ray source 5, which emanates X-ray radiation 17, which passes the first object 14 and the second object 13 and generates a projection image 26 of the first object 14 and the second object 13. The determination unit 9 determines the line of sight 25, which connects the first object, i.e. the catheter tip in this embodiment, on the two-dimensional projection images 26 with the X-ray source 5, i.e. with the region where the rays emanate. The determination 9 transmits this line of sight 25 to the visualization unit 12, and on the imaging region 22 of the visualization unit 12 the three-dimensional model of the second object 13 and the light of sight 25 are displayed after the three-dimensional model 20 has together with the line of sight 25 have been rotated, in order to allow viewing the line of sight 25 intersecting the three-dimensional model 20 from a side view. The determination unit 9 further determines the intersection points 27, 28 of the line of sight 25 with the three-dimensional model 20. The intersection points 27, 28 are also displayed on the imaging region 22. FIG. 3 shows in the left part the imaging region 22 displaying the three-dimensional model 20 and the registered two-dimensional projection image 26 before the rotation of the three-dimensional model 20. The middle part of FIG. 3 shows the imaging region 22 displaying the rotated three-dimensional model 20, the rotated line of sight 25, the two-determined intersection points 27, 28 and two imaginary catheters and catheter tips. The apparatus 1 for determining a position of a first object within a second object further comprises a selection unit 10 for selecting which of the two intersection points 27, 28 of the line of sight 25 with the three-dimensional model 20 corresponds to the position of the contact region. The selection unit preferentially comprises an input unit 11, like a mouse or a keyboard, which allows a user inputting signals into the selection unit 10 for selecting one of the intersection points 27, 28 as the contact region. That is, the intersection point selected by the user is regarded as being the contact region and, therefore the three-dimensional position of the first object 14 within the second object 13, i.e., in this embodiment, the position of the catheter tip 14 on the inner wall of the heart 13. This determined three-dimensional position 29 of the first object 14 within the second object 13 is displayed together with the three-dimensional model 20 on the imaging region 22 (right part of FIG. 3).

Figure 4A:
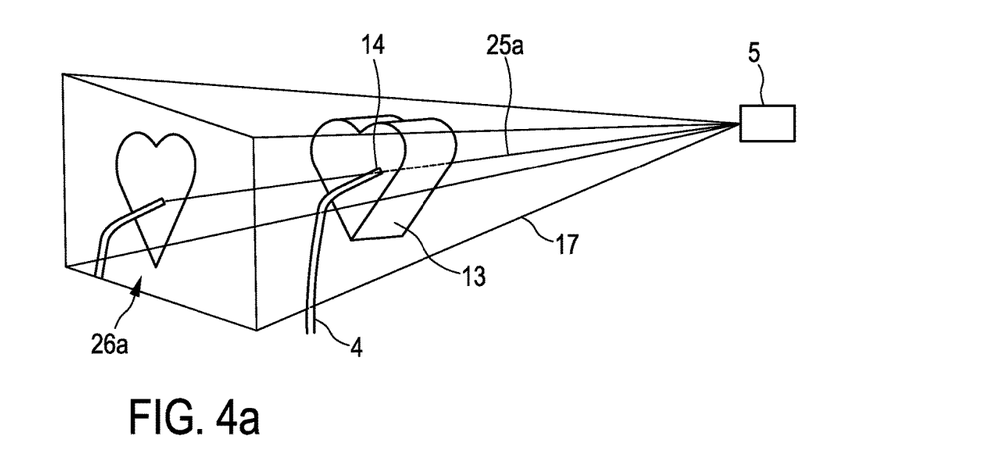
FIG. 4a shows schematically the generation of a first two-dimensional projection image in a first projection direction.
Figure 4B:
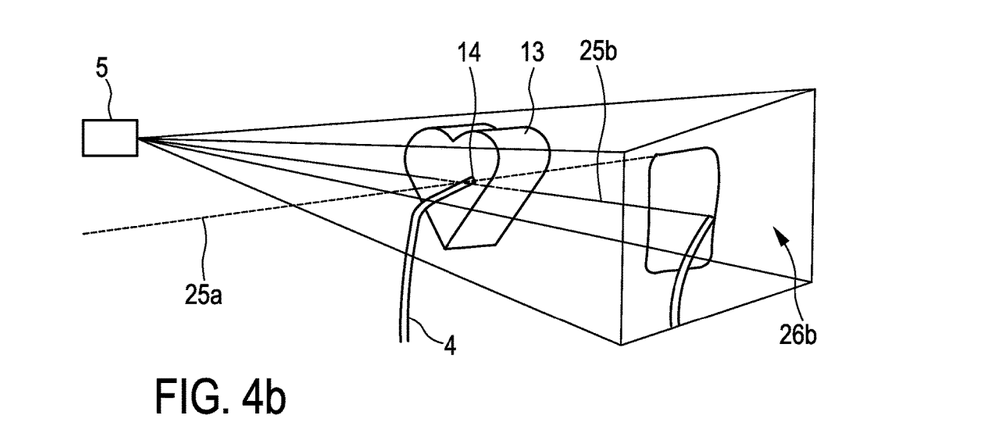
FIG. 4b shows schematically the generation of a second two-dimensional projection image in a second projection direction.

In another embodiment, the determination unit 9 can be adapted such that the contact region can be determined as described in the following with reference to FIG. 4a and 4b. In FIG. 4a a first two-dimensional projection image 26a is generated with respect to a first projection direction, and the determination unit 9 determines a first line of sight 25a. In FIG. 4b the projection unit has been rotated, for example, by an angle of 90°, a second two-dimensional projection image 26b is generated and the determination unit 9 determines a second line of sight 25b. In order to rotate the projection unit, the projection unit is preferentially mounted on a C-arm. The determination unit 9 determines the intersection point of the first line of sight 25a and of the second line of sight 25b and moves this intersection point onto the surface of the three-dimensional model 20 of the second object 13, which is contacted by the first object 14. The intersection point is not located on the surface of the three-dimensional model 20 of the second object 13, because of inaccuracies of measurements, a non-perfect alignment and a possible motion of the second object 13. Thus, only after the movement onto the surface of the three-dimensional model 20 of the second object 13 the moved determined intersection point of the two line of sights 25a, 25b is located on the surface of the three-dimensional model 20. This moved intersection point corresponds to the position of the contact region of the first object 14 and the second object 13 and therefore to the position of the first object 14 within the second object 13, i.e. the position of the moved intersection point is the determined three-dimensional position of the first object 14 within the second object 13. The three-dimensional model 20 of the second object 13 can be displayed on the imaging region 22 together with the determined three-dimensional position of the first object 14. The movement onto the surface of the three-dimensional model is preferentially preformed along the shortest distance between the determined intersection point and the surface of the three-dimensional model.

Figure 5:
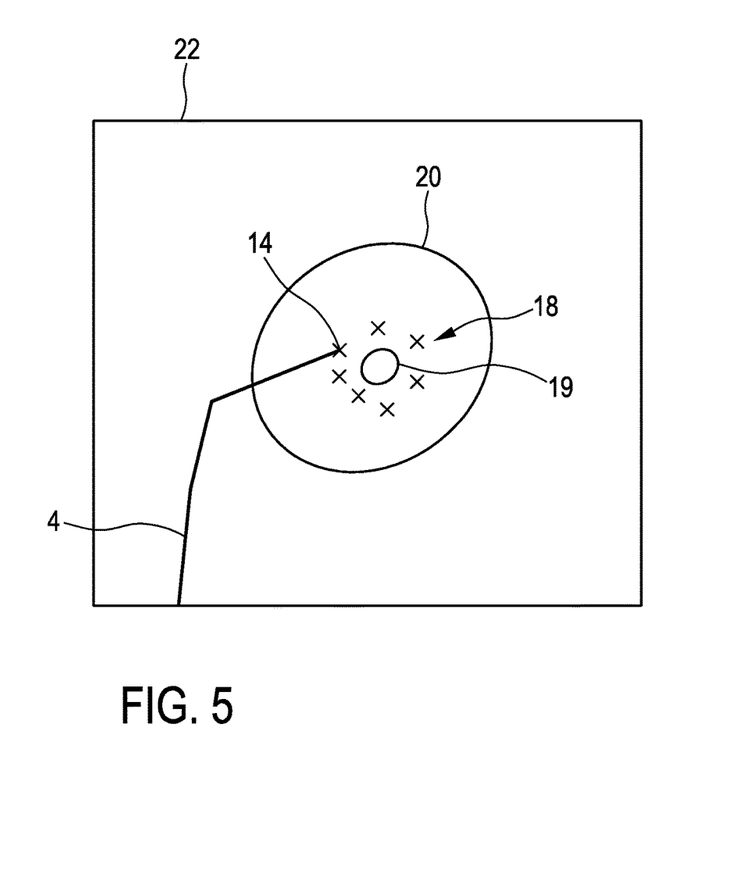
FIG. 5 shows schematically the imaging region showing different determined positions on the three-dimensional model of the second object.

As already mentioned above, in this embodiment the first object 14 is a catheter tip and the second object 13 is a heart of a patient. The catheter tip 14 can successively contact the inner wall of the heart 13 at different contact regions, for example, to denaturize heart tissue at the different contact regions for an ablation procedure. The apparatus 1 can be adapted such that each position of these contact regions, i.e., in this embodiment, each three-dimensional position of the catheter tip 14 on the inner wall of the heart 13, is determined and that each of the determined three-dimensional positions is marked by, for example, a cross or sphere on the three-dimensional model 20 of the heart. FIG. 5 shows these crosses 18 on the imaging region 22 together with the three-dimensional model 20, the catheter 4 and the catheter tip 14. FIG. 5 shows further schematically an ostium 19 of a pulmonary vein, which is surrounded by the determined positions 18, which, in this embodiment, correspond to ablation points.

If the projection unit is an X-ray fluoroscopy unit, the determination of the three-dimensional position of the first object within the second object can be performed such the total skin dose provided by the X-ray fluoroscopy remains significantly below any threshold for deterministic radiation effects, i.e. significantly below 2 Gy.

For determining a line of sight, the position of the first object on the two-dimensional projection image has to be determined. This determination can be performed automatically, for example, by thresholding or by pattern recognition using image processing. If, in this embodiment, the first object 14 is a catheter tip comprising metal, the position of the catheter tip 14 within the two-dimensional projection image can easily be determined by thresholding. In addition, for correction purposes or alternatively, a user can input a position within the two-dimensional projection image, wherein for the following determination of the respective line of sight this inputted position is regarded as being the position of the first object 14 on the two-dimensional projection image.

The visualization unit 12 is preferentially adapted such that the three-dimensional model 20 of the second object 13 is shown in a so-called "inverse perspective" that shows the three-dimensional model 20 as if it is projected by the same X-ray beam shape, which is preferentially a cone, that actually created the two-dimensional projection image from the second object 13.

Figure 6:
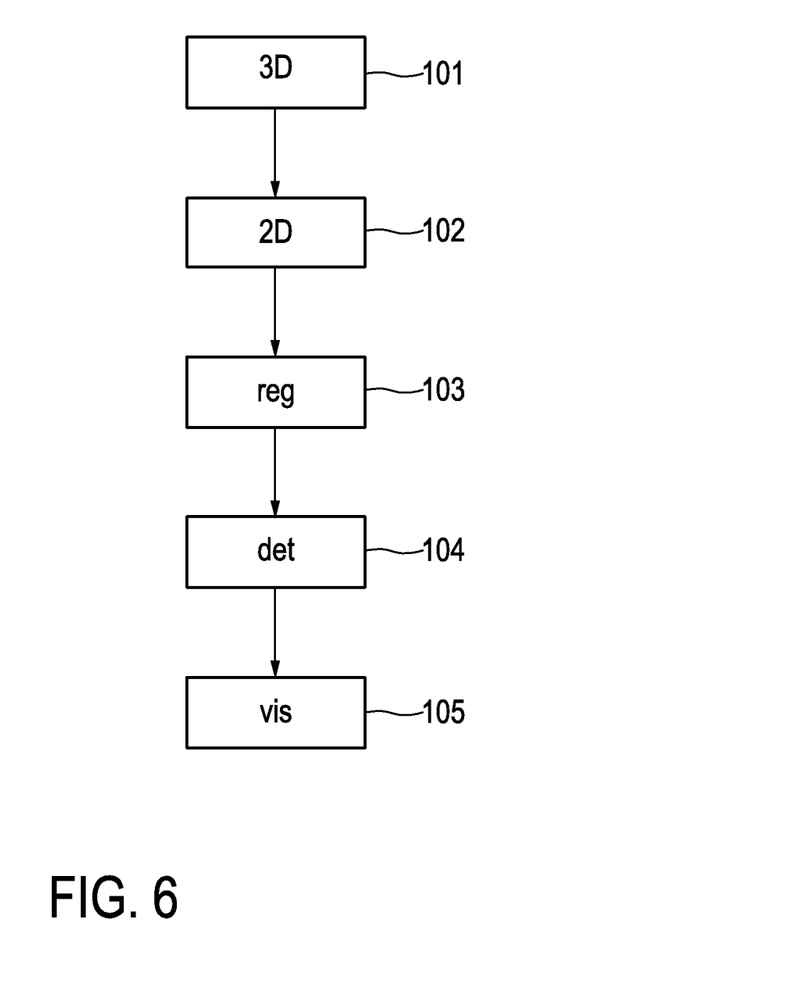
FIG. 6 shows schematically a flowchart illustrating an embodiment of a method for determining a position of a first object within a second object.

In the following a method for determining a position of a first object within a second object in accordance with the invention will be described with reference to a flowchart shown in FIG. 6.

In step 101 a three-dimensional model 20 of the second object 13 is provided. Furthermore, in step 102 a two-dimensional projection image of the first object 14 and of the second object 13 is generated. In step 103 the three-dimensional model 20 of the second object 13 is registered with the two-dimensional projection image. In step 104 the determination unit determines the contact region between the first object 14 and the second object 13 as the three-dimensional position of the first object 14 within the second object 13. The three-dimensional model 20 together with the determined three-dimensional position of the first object 14 within the second object 13 is displayed on the visualization unit 12 in step 105.

The above mentioned embodiments describe a first object which contacts a second object only at one contact region at a time. But the invention is not limited to such an arrangement. For example, the first object can comprise several parts, which contact the second object simultaneously. For example, if the first object is an ablation catheter and if the second object is a heart of a patient, the ablation catheter can comprise several electrodes or other catheter sites, which can contact an inner wall of the heart simultaneously, wherein the apparatus for determining a position of a first object within a second object is adapted such that for each of these parts of the ablation catheter the three-dimensional position on the inner wall of the heart can be determined.

Although, the invention has mainly been described with reference to a heart of a patient as being the second object, the invention is not limited to the determination of a position within a heart of a patient. For example, the second object can also be a technical object like a pipeline, wherein, for example, energy has to be applied to inner parts of the technical object for treatment purposes, wherein an energy emitting element is used within the technical object for applying the energy and wherein the position of the energy emitting element within the technical object has to be determined.

In the above described embodiments, the visualization unit comprises one imaging region. But the invention is not limited to only one imaging region of the visualization unit. For example, the visualization unit can also comprise more than two imaging regions. Furthermore, in accordance with the invention, in other embodiments, the or each imaging region could display the two-dimensional projection image and/or the three-dimensional model of the second object and/or the determined position of the first object within the second object.

The three-dimensional model can also be provided from the generation of the two-dimensional projection images, for example, by determining images of the second object during the generation of the two-dimensional projection images from different directions.

Some or all of the above described units can be implemented by one or several units. Furthermore, the units performing calculations and/or determinations like, for example, the determination unit, the registration unit or a reconstruction unit, can be program code means, which perform the respective functions and which can be run on a computer system, or dedicated hardware, which perform the respective functions.

The apparatus 1 for determining a position of a first object within a second object in combination with the catheter tip 14, the catheter 4 and the ablation and sensing unit 3 can be regarded as an apparatus for applying energy to a second object via a surface of the second object by using an energy emitting first object in accordance with the invention, wherein the energy emitting first object is the catheter tip, which might be an electrode, for applying energy to a second object via a surface of the second object like an inner wall of a heart of a patient.

Although, in the above described embodiment, the position of the catheter tip 14, which is connected to an ablation and sensing unit 3 via the catheter 4, has been determined within the second object 13, the apparatus for determining a position of a first object within a second object can also be used to determine the position of one or more other arbitrarily chosen first objects, which are located on a surface of a arbitrarily chosen second object.

Other variations to the disclosed embodiments can be understood and effected by those skilled in the art and practicing the claimed invention from the study of the drawing of the disclosure, and the appended claims.

While the invention has been illustrated and described in detail in the drawings and in the foregoing description, such illustration and description are to be considered illustrative or exemplary and not restrictive. The invention is not limited to the disclosed embodiments.

In the claims the word "comprising" does not exclude other elements or steps and the indefinite article "a" or "an" does not exclude a plurality. For example, in claim 1 also two or more two-dimensional projection images can be used for determining the position of the contact region.

A computer program may be stored/distributed on a suitable medium, such as an optical storage medium or a solid-state medium supplied together with or is part of other hardware, but may also distributed in other forms, such as the internet or other wired or wireless telecommunication systems.

Any reference signs in the claims should not be construed as limiting the scope of the invention.

The invention claimed is:

1. An apparatus for determining a position of a first object within a second object, wherein the first object contacts the second object at a contact region, the apparatus comprising:
   a provision unit for providing a three-dimensional model of the second object,
   a projection unit for generating a two-dimensional projection image of the first object and of the second object,
   a registration unit for registering the three-dimensional model with the two-dimensional projection image subsequent to the generation of the two-dimensional projection by the projection unit,
   a determination unit for determining the position of the contact region from the position of the first object on the two-dimensional projection image and the registered three-dimensional model of the second object, the position of the contact region being the position of the first object within the second object,
   wherein the determination unit is adapted such that the position of the contact region is determined by determining the position where a line of sight of the first object intersects a surface of the three-dimensional model of the second object.

2. The apparatus as claimed in claim 1, wherein the projection unit is adapted for generating two-dimensional projection images in different projection directions, and
   wherein the registration unit is adapted for registering the three-dimensional model with the different two-dimensional projection images subsequent to the generation of the different two-dimensional projection images by the projection unit such that in each of the different projection directions the three-dimensional model is registered with the corresponding two-dimensional projection image.

3. The apparatus as claimed in claimed 1, wherein the apparatus further comprises a selection unit for selecting which of two or more intersection points of the line of sight with the three-dimensional model corresponds to the position of the contact region.

4. The apparatus as claimed in claimed 3,
   wherein the apparatus comprises an visualization unit for visualizing the three-dimensional model, the line of sight and the two or more intersection points from a side view, and
   wherein the selection unit comprises an input unit allowing a user selecting one of the intersection points as the position of the contact region.

5. The apparatus as claimed in claim 3,
   wherein the projection unit is adapted for generating at least two two-dimensional projection images of the first object and of the second object in at least two projection directions,
   wherein the registration unit is adapted for registering the three-dimensional model with the at least two two-dimensional projection images subsequent to the generation of the at least two two-dimensional projection images by the projection unit,
   wherein the determination unit is adapted for determining the position of the contact region where a line of sight of the first object with respect to a projection direction of one of the two-dimensional projection images intersects the three-dimensional model, and
   wherein the selection unit is adapted for selecting which of the two or more intersection points of the line of sight with the three-dimensional model corresponds to the position of the contact region by using at least one of the other two-dimensional projection images.

6. The apparatus as claimed in claim 1,
   wherein the projection unit is adapted for generating at least two two-dimensional projection images of the first object and of the second object in at least two projection directions,
   wherein the registration unit is adapted for registering the three-dimensional model with the at least two two-dimensional projection images subsequent to the generation of the at least two two-dimensional projection images by the projection unit,
   wherein the determination unit is adapted for determining at least two line of sights of the first object for the at least two projection directions,
   wherein the determination unit is further adapted for determining the intersection point of the at least two line of sights,
   wherein the determination unit is further adapted for moving the intersection point onto a surface of the three-dimensional model, and
   wherein the moved intersection point is the determined position of the contact region.

7. The apparatus as claimed in claim 1,
   wherein the apparatus comprises a visualization unit for visualizing the three-dimensional model over the two-dimensional projection image, and
   wherein the visualization unit is adapted for showing the three-dimensional model, the two-dimensional projection image and the determined position of the first object simultaneously.

8. The apparatus as claimed in claim 7, wherein the visualization unit is adapted such that the determined position of the first object is visualized by a graphical indication on the three-dimensional model.

9. The apparatus as claimed in claim 7, wherein the visualization unit comprises an imaging region for visualizing the three-dimensional model over the two-dimensional projection image.

10. The apparatus as claimed in claim 1,
    wherein the provision unit is adapted for providing a moving three-dimensional model of the second object,
    wherein the apparatus further comprises a motion detection unit for detecting the motion of the second object during generating the two-dimensional projection image of the first object and of the second object by the projection unit, and
    wherein the registration unit is adapted for registering the moving three-dimensional model with the two-dimensional projection image subsequent to the generation of the two-dimensional projection image by the projection unit.

11. The apparatus as claimed in claim 1, wherein the first object is operable for applying energy to the second object.

12. A method for determining a position of a first object within a second object, wherein the first object contacts the second object at a contact region, the method comprising following steps:
    providing a three-dimensional model of the second object,
    generating, by a projection unit, a two-dimensional projection image of the first object and of the second object, registering the three-dimensional model with the two-dimensional projection image subsequent to the generation of the two-dimensional projection image by the projection unit, determining the position of the at least one contact region from the position of the first object on the two-dimensional projection image and the registered three-dimensional model of the second object, the position of the at least one contact region being the position of the first object within the second object, wherein the position of the contact region is determined by determining the position where a line of sight of the first object intersects a surface of the three-dimensional model of the second object.

13. The method as claimed in claim 12, wherein the generating by the projection unit of the two-dimensional projection image of the first object and of the second object includes generating, by the projection unit, two-dimensional projection images in different projection directions, and wherein registering the three-dimensional model with the two-dimensional projection image includes registering the three-dimensional model with the different two-dimensional projection images subsequent to the generation of the different two-dimensional projection images by the projection unit such that in each of the different projection directions the three-dimensional model is registered with the corresponding two-dimensional projection image.

14. The method as claimed in claimed 12, further comprising selecting which of two or more intersection points of the line of sight with the three-dimensional model corresponds to the position of the contact region.

15. The method as claimed in claimed 14, further comprising visualizing the three-dimensional model, the line of sight and the two or more intersection points from a side view, wherein selecting which of two or more intersection points of the line of sight with the three-dimensional model corresponds to the position of the contact region includes allowing a user to select one of the intersection points as the position of the contact region.

16. The method as claimed in claim 14, wherein the generating by the projection unit of the two-dimensional projection image of the first object and of the second object includes generating, by the projection unit, at least two two-dimensional projection images of the first object and of the second object in at least two projection directions, wherein registering the three-dimensional model with the two-dimensional projection image includes registering the three-dimensional model with the at least two two-dimensional projection images subsequent to the generation of the at least two two-dimensional projection images by the projection unit, wherein determining the position of the at least one contact region from the position of the first object on the two-dimensional projection image and the registered three-dimensional model of the second object includes determining the position of the contact region where a line of sight of the first object with respect to a projection direction of one of the two-dimensional projection images intersects the three-dimensional model, and wherein selecting which of two or more intersection points of the line of sight with the three-dimensional model corresponds to the position of the contact region includes selecting which of the two or more intersection points of the line of sight with the three-dimensional model corresponds to the position of the contact region by using at least one of the other two-dimensional projection images.

17. The method as claimed in claim 12, wherein the generating by the projection unit of the two-dimensional projection image of the first object and of the second object includes generating, by the projection unit, at least two two-dimensional projection images of the first object and of the second object in at least two projection directions, wherein registering the three-dimensional model with the two-dimensional projection image subsequent to the generation of the at least two two-dimensional projection images by the projection unit includes registering the three-dimensional model with the at least two two-dimensional projection images, wherein determining the position of the at least one contact region from the position of the first object on the two-dimensional projection image and the registered three-dimensional model of the second object includes:

determining at least two line of sights of the first object for the at least two projection directions, determining the intersection point of the at least two line of sights, and moving the intersection point onto a surface of the three-dimensional model, wherein the moved intersection point is the determined position of the contact region.

18. The method as claimed in claim 12, further comprising:

visualizing the three-dimensional model over the two-dimensional projection image and showing the three-dimensional model, the two-dimensional projection image and the determined position of the first object simultaneously.

19. The method as claimed in claim 18, wherein the determined position of the first object is visualized by a graphical indication on the three-dimensional model.

20. The method as claimed in claim 12, further comprising:

moving the three-dimensional model of the second object, detecting the motion of the second object during the generating by the projection unit of the two-dimensional projection image of the first object and of the second object, and wherein registering the three-dimensional model with the two-dimensional projection image subsequent to the generation of the two-dimensional projection image by the projection unit includes registering the moving three-dimensional model with the two-dimensional projection image.

* * * * *